(12) United States Patent
Qin et al.

(10) Patent No.: US 11,642,667 B2
(45) Date of Patent: May 9, 2023

(54) MULTI-SANDWICH COMPOSITE CATALYST AND PREPARATION METHOD AND APPLICATION THEREOF

(71) Applicant: Institute of Coal Chemistry, Chinese Academy of Sciences, Shanxi (CN)

(72) Inventors: Yong Qin, Taiyuan (CN); Bin Zhang, Taiyuan (CN); Huibin Wu, Taiyuan (CN); Haojie Liang, Taiyuan (CN)

(73) Assignee: Institute of Coal Chemistry, Chinese Academy of Sciences, Shanxi (CN)

( * ) Notice: Subject to any disclaimer, the term of this patent is extended or adjusted under 35 U.S.C. 154(b) by 0 days.

(21) Appl. No.: 17/044,702

(22) PCT Filed: May 14, 2020

(86) PCT No.: PCT/CN2020/090259
§ 371 (c)(1),
(2) Date: Oct. 1, 2020

(87) PCT Pub. No.: WO2020/228779
PCT Pub. Date: Nov. 19, 2020

(65) Prior Publication Data
US 2022/0280929 A1    Sep. 8, 2022

(30) Foreign Application Priority Data
May 14, 2019    (CN) .......................... 201910397681.2

(51) Int. Cl.
*B01J 35/06*    (2006.01)
*B01J 23/89*    (2006.01)
(Continued)

(52) U.S. Cl.
CPC ............. *B01J 35/06* (2013.01); *B01J 23/892* (2013.01); *B01J 37/0018* (2013.01);
(Continued)

(58) Field of Classification Search
None
See application file for complete search history.

(56) References Cited

FOREIGN PATENT DOCUMENTS

| CN | 101214444 | 7/2008 |
| CN | 105771972 | 7/2016 |

(Continued)

OTHER PUBLICATIONS

Ge, et al., "A Tandem Catalyst with Multiple Metal Oxide Interfaces Produced by Atomic Layer Deposition", Angewandte Chemie International Edition, 55, Wiley-VCH Verlag GmbH & Co., 2016, pp. 7081-7085.

(Continued)

*Primary Examiner* — Colin W. Slifka
(74) *Attorney, Agent, or Firm* — DLA Piper LLP (US)

(57) ABSTRACT

The present disclosure relates to a multi-sandwich composite catalyst and a preparation method and application thereof. The present disclosure provides a preparation method of a multi-sandwich composite catalyst, comprises the following steps: sequentially depositing a first layer oxide, a first active metal, an oxide interlayer, a second active metal and a surface oxide on a template, and sequentially performing calcination and reduction, thereby obtaining a multi-sandwich composite catalyst; wherein the first active metal and the second active metal are different kinds of active metals. In the present disclosure, a multi-sandwich structure is formed by depositing the oxides and active metals alternately, so that the position and spacing distance of the active centers can be precisely controlled. The multi-sandwich composite catalyst prepared by the method provided described herein has a higher conversion than that of a catalyst without an interlayer when used for the catalytic reaction.

20 Claims, 1 Drawing Sheet

(51) Int. Cl.
   *B01J 37/00* (2006.01)
   *B01J 37/02* (2006.01)
   *B01J 37/08* (2006.01)
   *B01J 37/18* (2006.01)
   *B01J 37/34* (2006.01)
   *C01B 3/04* (2006.01)
   *C07C 209/36* (2006.01)

(52) U.S. Cl.
   CPC ......... *B01J 37/0215* (2013.01); *B01J 37/082* (2013.01); *B01J 37/18* (2013.01); *B01J 37/348* (2013.01); *C01B 3/04* (2013.01); *C07C 209/36* (2013.01); *C01B 2203/0277* (2013.01); *C01B 2203/107* (2013.01)

(56) References Cited

FOREIGN PATENT DOCUMENTS

| | | |
|---|---|---|
| CN | 105817270 | 8/2016 |
| CN | 105903480 | 8/2016 |
| CN | 108262055 | 7/2018 |
| CN | 110038590 | 7/2019 |

OTHER PUBLICATIONS

Zecevic, et al., "Nanoscale intimacy in bifunctional catalysts for selective conversion of hydrocarbons", Nature, vol. 528, Macmillan Publishers Limited, Dec. 10, 2015, pp. 245-254.

MULTI-SANDWICH COMPOSITE CATALYST AND PREPARATION METHOD AND APPLICATION THEREOF

CROSS-REFERENCE TO RELATED APPLICATIONS

This application is the National Stage filing under 35 U.S.C. 371 of International Application No. PCT/CN2020/090259, filed May 14, 2020, which claims priority to Chinese patent application number 201910397681.2, filed May 14, 2019, which is titled "Multi-sandwich composite catalyst and preparation method and application thereof", which are incorporated by reference in their entireties.

TECHNICAL FIELD

The invention belongs to the technical field of catalyst materials, and in particular relates to a multi-sandwich composite catalyst and a preparation method and application thereof.

BACKGROUND

With the continuous strengthening of energy conservation and environmental awareness, people have put forward new requirements for the green development of chemistry. The development of new chemical processes that are more efficient, energy-saving and pollution-free has become a hot spot of attention. For this reason, attempts are being made to couple several different types of reactions, and it is hoped that a one-step tandem reaction can be used to achieve high efficiency and energy savings.

However, the tandem reaction requires the catalyst to be compatible with the raw materials, solvents, intermediates and reaction conditions of different reactions. The design and construct of the catalyst structure to be compatible with the tandem reaction, the efficient matching, and the coupling of the multifunctional catalytic centers become issues to address.

Recent studies have shown that the distance between different active sites has an influence on the catalytic performance of the tandem reaction catalyst. The distance of the active site affects the electron density and charge transfer of the active sites on the catalyst surface and the transfer of intermediate species during the catalytic reaction, which in turn affects the catalytic activity and selectivity. In 2015, Krijn P. de Jong et al. found in the study of the cracking reaction of long-chain alkanes that the moderate distance between metal platinum and molecular sieves is beneficial to improving the selectivity of the ideal product isoparaffin. When the distance is too small, it can be easy to produce by-products of pyrolysis small molecular alkanes. When it is too far, it is easy to deposit carbon on the surface of the molecular sieves, which is not conducive to the reaction (Nature 2015, 528, 245-248). In 2017, Peng Gao et al. studied the reaction of $CO_2$ hydrogenation to produce hydrocarbon products and found that the mechanically mixed $In_2O_3$ and ZSM-5 molecular sieves are suitable for the formation of the ideal product $C_{5+}$ when the distance is moderate. Too close or too far of a distance is easy to produce by-product methane (CN108262055A). In addition, the appropriate construction of space-separated tandem catalysts can improve the tandem catalytic performance. In 2016, Qin Yong's team of the Institute of Coal Chemistry Chinese Academy of Sciences used the template method and the sacrificial layer strategy to prepare the tube-in-tube structure metal-oxide double-interface tandem catalyst, and found the interface synergy mechanism (Angew. Chem. Int. Ed. 2016, 55, 7081-7085; CN105817270A, CN105903480A), but this method still does not achieve precise control of the distance between the two functional centers.

SUMMARY

The present disclosure aims to provide a preparation method of a multi-sandwich composite catalyst, and the method provided by the present disclosure can precisely control the distance between different active sites, thereby obtaining a tandem catalyst which satisfies different catalytic reactions.

In order to achieve the above object, the present disclosure provides the following technical solutions:

The present disclosure provides a preparation method of a multi-sandwich composite catalyst, which comprises: sequentially depositing a first oxide layer, a first active metal, an oxide interlayer, a second active metal and a surface oxide layer on a template, and then sequentially performing calcination and reduction, thereby obtaining a multi-sandwich composite catalyst; the first active metal and the second active metal are different kinds of active metals.

In some embodiments, the method for preparing the template comprises: spreading a dispersion of a carrier on a substrate, removing the dispersant, and obtaining a template; the carrier comprises one or more selected from the group consisting of carbon nanotubes, carbon nanofibers, aluminum oxide nanowires, porous aluminum oxide spheres, zinc oxide nanowires, zinc oxide nanorods, and iron oxide nanofibers.

In some embodiments, the metallic elements in the first active metal layer and the second active metal layer are independently nickel, platinum, palladium, rhodium, cobalt, copper or iron.

In some embodiments, the number of cycles of the first active metal and the second active metal deposition is independently 5-500.

In some embodiments, the number of cycles of the first layer oxide and the surface oxide deposition is independently 10-500, and the number of cycles of the oxide interlayer deposition is 1-90.

In some embodiments, the calcination temperature is 250-900° C., and the calcination time is 0.5-6 h.

In some embodiments, the reducing reagent for reduction is a mixed gas of hydrogen and argon; the reduction temperature is 250-900° C., and the reduction time is 1-6 hours.

The present disclosure provides a multi-sandwich composite catalyst comprising, in order from the inside to the outside, a first oxide layer, a first active metal layer, an oxide interlayer, a second active metal layer and a surface oxide layer; the metal in the first active metal layer and the second active metal layer are different kinds of active metals.

In some embodiments, the multi-sandwich composite catalyst comprises $TiO_2/Ni/TiO_2/Pt/TiO_2$ composite catalyst, $ZrO_2/Ni/ZrO_2/Pd/ZrO_2$ composite catalyst, $TiO_2/Ni/ZnO/Pt/TiO_2$ composite catalyst, $TiO_2/Ni/Al_2O_3/Pt/TiO_2$ composite catalyst, $TiO_2/Ni/Ga_2O_3/Pt/TiO_2$ composite catalyst, $Al_2O_3/Pd/Al_2O_3/Rh/Al_2O_3$ composite catalyst, $CeO_2/Pt/Al_2O_3/Co/SiO_2$ composite catalyst or $TiO_2/Cu/Ga_2O_3/Fe/TiO_2$ composite catalyst.

The present disclosure further provides the use of the multi-sandwich composite catalyst described in the above technical solution in the tandem catalytic reaction.

The present disclosure provides a preparation method of a multi-sandwich composite catalyst, which comprises sequentially depositing a first layer oxide, a first active metal, an oxide interlayer, a second active metal and a surface oxide on a template, and then sequentially performing calcination and reduction, thereby obtaining a multi-sandwich composite catalyst; the first active metal and the second active metal are different kinds of active metals. The present disclosure forms a multi-sandwich structure by alternately depositing oxides and active metals, so that the position and separation distance of the active centers are precisely controlled. The results of embodiments show that the multi-sandwich composite catalyst prepared by the method provided by the present invention has a better conversion rate than that of a catalyst without an oxide interlayer when used for catalytic reaction.

DESCRIPTION OF THE EMBODIMENTS

The present disclosure provides a preparation method of a multi-sandwich composite catalyst, which comprises: sequentially depositing a first layer oxide, a first active metal, an oxide interlayer, a second active metal and a surface oxide on a template, and then sequentially performing calcination and reduction, thereby obtaining a multi-sandwich composite catalyst; the first active metal and the second active metal are different kinds of active metals.

In the present disclosure, the method for preparing the template preferably includes:

Coating a dispersion of the carrier on a substrate, and removing the dispersant to obtain the template.

In the present disclosure, the carrier preferably comprises one or more selected from the group consisting of carbon nanotubes, carbon nanofibers, aluminum oxide nanowires, porous aluminum oxide spheres, zinc oxide nanowires, zinc oxide nanorods, and iron oxide nanofibers, and more preferably carbon nanotubes and/or carbon nanofibers. The present disclosure has no particular requirements for the size of the carrier, and a commercially available product well known to those skilled in the art may be used.

The present disclosure has no special requirements on the material of the substrate, and may be made of materials well known to those skilled in the art, such as glass sheet.

In the present disclosure, the dispersion of the carrier can use organic solvent or water as a dispersant, and the organic solvent preferably includes one or more selected from the group of ethanol, acetone, carbon tetrachloride, n-hexane, diethyl ether, isopropanol and methanol. In the dispersion, the mass ratio of the carrier to the dispersant is preferably 1:(3-20), more preferably 1:(5-10). The present disclosure has no particular requirements for the coating method and coating amount of the dispersion, and it is well known to those skilled in the art.

After the dispersion of the carrier is applied to the substrate, the embodiments of the present disclosure dry the substrate on which the dispersion is applied to remove the solvent to obtain a template. The present disclosure has no special requirements for the drying method and can be naturally dried in the air.

After the template is obtained, embodiments of the present disclosure can place the template in a deposition chamber to adjust various parameters of the deposition chamber to provide conditions for subsequent multi-step depositions. In the present disclosure, the deposition is preferably atomic layer deposition, and the deposition chamber is preferably an atomic layer deposition vacuum reaction chamber (ALD reaction chamber); the parameters to be adjusted preferably include chamber temperature, chamber pressure, and carrier gas flow rate, the chamber temperature is preferably 50-400° C., more preferably 90-300° C.; the chamber pressure is preferably 10-200 Pa, more preferably 50-150 Pa; the carrier gas flow rate is preferably in accordance with the volume ratio of the carrier gas to the atomic layer deposition vacuum reaction chamber of 1/10-1/5 $min^{-1}$, and the carrier gas flow rate is kept in the same range throughout the deposition process. In embodiments of the present disclosure, the carrier gas is preferably an inert gas such as nitrogen, argon or helium.

In the present disclosure, the oxide preferably includes a metal oxide and a non-metal oxide, and the metal oxide preferably includes titanium oxide ($TiO_2$), aluminum oxide ($Al_2O_3$), zirconia ($ZrO_2$), zinc oxide (ZnO), cerium oxide ($CeO_2$), indium oxide ($In_2O_3$) or gallium oxide ($Ga_2O_3$); the non-metal oxide preferably comprises silicon oxide.

In the present disclosure, the first active metal and the second active metal are preferably independently nickel, platinum, palladium, rhodium, cobalt, copper or iron. In some embodiments, different active metals are selected for deposition according to different reactions. In some embodiments of the present disclosure, when the first active metal is nickel, the second active metal is preferably platinum or palladium; when the first active metal is palladium, the second active metal is preferably rhodium; when the first active metal is platinum, the second active metal is preferably cobalt.

In order to clearly describe the deposition process of the present technical solution, embodiments of the present disclosure divide the components into the first layer oxide, the oxide interlayer and the surface oxide according to the deposition order, and the component selection range of each layer oxide is same with that of the oxide of the above technical solution and the oxide components of different layers may be the same or different. Based on the above description, the deposition process of the present technical solution is described as follows:

After the template is obtained, embodiments of the present disclosure firstly deposit a first layer oxide on the template. In the deposition of the first layer oxide, embodiments of the present disclosure preferably use a component having a vapor pressure as a precursor. Specifically, the deposition of titanium oxide preferably uses titanium isopropoxide and water as the precursor; the deposition of aluminum oxide preferably uses trimethylaluminum and water as the precursor; the deposition of zirconia preferably uses zirconium tert-butoxide and water as the precursor; the deposition of zinc oxide preferably uses organic zinc and water as the precursor, and the organic zinc preferably comprises diethyl zinc or dimethyl zinc; the deposition of cerium oxide preferably uses tris(isopropylcyclopentadienyl) cerium and ozone as the precursor; the deposition of indium oxide preferably uses trimethylindium and water as the precursor; the deposition of gallium oxide preferably uses triethyl gallium and water as the precursor; the deposition of silicon oxide preferably uses silicone and ozone as the precursor, and the silicone preferably includes tris(dimethylamino)silane or tetraethyl orthosilicate.

In the present disclosure, when the first layer oxide is deposited, the temperature of the ALD reaction chamber is preferably 150-300° C., more preferably 175-225° C., most preferably 180-200° C. In the deposition of the first layer oxide of the present disclosure, the deposition process preferably comprises pulsing the precursor vapor corresponding to the first layer oxide into the deposition chamber, and after diffusion and purging, pulsing water vapor into the deposition chamber, and then performing diffusion and purging to complete a deposition cycle (ALD cycle), and repeating the above steps to complete the deposition of the first layer oxide.

According to some embodiments of the present disclosure, the temperature of the first layer oxide precursor vapor is preferably 80-100° C., more preferably 80-90° C.; and the temperature of the water vapor is preferably 10-40° C., more preferably 20-30° C. When depositing, the pulse time of the first layer oxide precursor vapor is preferably 1-2 s, more preferably 1 s; the diffusion time is preferably 7-10 s, more preferably 8-9 s; and the purge time is preferably 18-25 s, more preferably 20-22 s, most preferably 20 s; when pulsing the water vapor, the pulse time is preferably 0.1-0.2 s, more preferably 0.1 s; the diffusion time is preferably 7-10 s, more preferably 8-9 s; the purge time is preferably 22-27 s, more preferably 24-25 s.

In some embodiments of the present disclosure, taking the oxide precursor and the water vapor completing one pulse-purging as one cycle, when depositing a first layer oxide, the number of cycles of deposition is preferably 10-500, more preferably 200-350, most preferably 280-320. After the cyclic deposition is completed, the first oxide layer is formed.

After depositing the first layer oxide, embodiments of the present disclosure deposit a first active metal on the surface of the first layer oxide. In the present disclosure, the first active metal means a metal having catalytic activity; and the active metal preferably includes nickel, platinum, palladium, rhodium, cobalt, copper or iron. In the present disclosure, the first active metal deposition component is an oxide corresponding to the active metal. Specifically, when the first active metal is nickel, the deposited material is nickel oxide; when the first active metal is platinum, the deposited material is a platinum oxide, and the remaining components are analogized in turn.

In some embodiments of the present disclosure, when depositing the first active metal, it is preferred to use a metal-organic complex having a vapor pressure as a precursor, and the temperature of the precursor is preferably 70-100° C., more preferably 75-85° C. In the present disclosure, the specific component of the precursor is preferably determined according to the kind of active metal to be deposited. In some embodiments, the deposition of nickel preferably uses nickelocene or nickel acetylacetonate as the precursor; the deposition of platinum preferably uses trimethylmethylcyclopentadienyl platinum (IV) or acetylacetonate platinum as the precursor; the deposition of rhodium preferably uses rhodium triacetylacetonate as the precursor; the deposition of copper oxide preferably uses bis(tert-butylacetylacetone) copper as the precursor; the deposition of iron oxide preferably uses ferrocene as the precursor; the deposition of palladium preferably uses palladium hexafluoroacetylacetonate as the precursor; the deposition of cobalt preferably uses cobaltocene as the precursor.

In some embodiments of the present disclosure, when depositing the first active metal, the temperature of the ALD chamber is preferably 150-500° C., more preferably 200-450° C., most preferably 200-300° C.; the deposition process preferably includes: pulsing the precursor vapor of the first active metal into the deposition chamber, and after diffusion and purging, pulsing the ozone into the deposition chamber, and then performing diffusion and purging to complete a deposition cycle (ALD cycle), and repeating the above steps to obtain a second metal oxide layer.

In some embodiments of the present disclosure, the pulse time of the first active metal precursor vapor is preferably 5-10 s, more preferably 6-8 s, most preferably 7 s; and the diffusion time is preferably 8-12 s, more preferably 9-11 s, most preferably 10 s; the purge time is preferably 22-27 s, more preferably 24-26 s, most preferably 25 s; and when pulsing ozone, the pulse time is preferably 1-2 s, more preferably 1 s; and the diffusion time is preferably 8-12 s, more preferably 9-11 s, most preferably 10 s; the purge time is preferably 22-27 s, more preferably 24-25 s, most preferably 25 s.

In some embodiments of the present disclosure, taking the first active metal precursor and the ozone respectively completing one diffusion-purging as one cycle, and when depositing the first active metal, the number of cycles of deposition is preferably 5-600, more preferably 10-500. The methods of the present disclosure preferably performs deposition under the above conditions, which is advantageous in obtaining nano-sized particles and a first active metal layer having a suitable thickness.

After depositing the first active metal, some embodiments of the present disclosure deposit an oxide interlayer on the surface of the first active metal layer; the oxide interlayer is deposited in a manner consistent with that of the deposition of the first layer oxide, and the number of cycles of the deposition is preferably determined based on the types of the two active metals and the type of reaction used. In the specific implementation of the present disclosure, the number of cycles of the oxide interlayer deposition is preferably 1-99, more preferably 3-95, most preferably 5-80.

In some embodiments of the present disclosure, when the oxide interlayer is titanium oxide, the number of cycles of the oxide interlayer deposition is preferably 10-40, more preferably 15-35, most preferably 20-30; when the oxide interlayer is zirconia, the number of cycles of the oxide interlayer deposition is preferably 5-30, more preferably 10-25, most preferably 15-20; when the oxide interlayer is aluminum oxide, the number of cycles of the oxide interlayer deposition is preferably 5-15, more preferably 7-12, most preferably 9-10.

In some embodiments of the present disclosure, when the first layer oxide, the oxide interlayer and the surface oxide are three different components, the number of cycles of the oxide interlayer deposition is preferably 20-40, more preferably 25-35, and most preferably 28-32.

After depositing the oxide interlayer, embodiments of the present disclosure deposit a second active metal on the surface of the oxide interlayer, and the component selection range of the second active metal is preferably the same as that of the first active metal described in the above technical solution. The deposition step is preferably the same as that of the surface oxide or the oxide interlayer described in the above technical solution, except the set of the deposition parameters, specifically, the pulse time of the second active metal precursor vapor is 0.3-0.7 s, more preferably 0.4-0.6 s, most preferably 0.5 s, and the diffusion time is preferably 8-12 s, more preferably 9-11 s, and most preferably 10 s, the purge time is preferably 20-27 s, more preferably 22-25 s, most preferably 25 s; the selection range of the pulse time, diffusion time and purge time of the ozone is the same with that of parameters used in the deposition of the surface oxide or oxide interlayer and will not be repeated here.

In some embodiments of the present disclosure, when depositing the second active metal, the number of cycles of deposition is preferably 5-600, more preferably 5-500, most preferably 10-300.

After depositing the second active metal, embodiments of the present disclosure deposit a surface oxide on the surface of the formed layer of the second active metal. In the present disclosure, the component selection range and the deposition process of the surface oxide are preferably the same as those of the first layer oxide and the interlayer described in the above technical solution and are not repeated here.

After depositing the surface oxide according to the present disclosure, the material for depositing the surface oxide is sequentially calcined and reduced to obtain a multi-sandwich composite catalyst. Prior to calcination, embodiments of the present disclosure preferably remove the template. In the present disclosure, when the carrier used in the preparation of the template is a nanotube, a nanowire, a nanorod or a fiber, the removal mode of the template preferably includes a calcination method or a dissolution reaction method; when the carrier used in the preparation of the template is porous aluminum oxide, the removal method of the template preferably includes a peeling method.

In some embodiments of the present disclosure, when the carrier used in the preparation of the template is a nanotube, a nanowire, a nanorod or a fiber, the removal mode of the template is preferably divided into the following two cases according to the material of the carrier.

First: when the carrier in the template is carbon nanotubes or carbon nanofibers, the removal method is preferably a calcination method. In some embodiments of the present disclosure, the calcination temperature is preferably 250-900° C., more preferably 300-800° C., most preferably 350-500° C.; and the heating rate to the above temperature is preferably 0.5-10° C./min, more preferably 1-8° C./min, most preferably 3-5° C./min; the calcination time is preferably 0.5-6 h, more preferably 1-5 h, most preferably 1.5-4 h; the calcination is preferably carried out under an air or oxygen atmosphere. In some embodiments of the present disclosure, when the carrier used for the template is carbon nanotubes or carbon nanofibers, the calcination step can remove the template while promoting crystallization and pore formation of the surface oxide.

Second: when the carrier in the template is aluminum oxide, zinc oxide or iron oxide, the removal method of the carrier is preferably a dissolution reaction method. In some embodiments of the present disclosure, the dissolution reagent used in the dissolution reaction method is selected as follows: an agent capable of reacting with a carrier component without reacting with other structural layer components. Specifically, when the carrier is aluminum oxide, if the first layer oxide is silicon oxide, the acidic reagent is selected to remove the carrier aluminum oxide, such as hydrochloric acid or sulfuric acid; if the first layer oxide is a metal oxide, the strong base reagent is selected to remove the carrier aluminum oxide, such as sodium hydroxide or potassium hydroxide.

In some embodiments of the present disclosure, when the carrier is a porous material, it is not necessary to remove the carrier, and only the substrate needs to be peeled off and removed. The present disclosure has no particular requirements for the manner of the peeling, and may be carried out in a manner well known to those skilled in the art.

After removing the template, embodiments of the present disclosure calcine the material after removing the template. In the present disclosure, the calcination temperature is preferably 250-900° C., more preferably 300-800° C., most preferably 350-500° C.; and the heating rate to the above temperature is preferably 0.5-10° C./min, more preferably 1-8° C./min, most preferably 3-5° C./min; the calcination time is preferably 0.5-6 h, more preferably 1-5 h, most preferably 1.5-4 h. It should be noted that when the template is removed by a calcination method, the reduction can be directly performed after the removal, and there is no need for re-calcination. Preferably, embodiments of the present disclosure involve calcination under the above conditions to make the first layer oxide, the oxide interlayer and the surface oxide form a porous structure, the pore diameter is 1-2 nm, and the specific surface area of the multi-sandwich composite catalyst obtained after the reduction is 60-120 m$^2$/g.

After calcination, embodiments of the present disclosure reduce the calcined material to obtain a multi-sandwich composite catalyst. In the present disclosure, the reducing agent for reduction is preferably a mixed gas of hydrogen and argon, and the volume of hydrogen in the mixed gas is preferably 1-100%, more preferably 3-50%, most preferably 5%; the temperature of reduction is preferably 250-900° C., more preferably 300-600° C., most preferably 350-500° C.; the heating rate to the above temperature is preferably 3-8° C./min, more preferably 4-6° C., most preferably 5° C./min; the time of reduction is preferably 1-6 h, more preferably 1.5-2.5 h, most preferably 2 h. Embodiments of the present disclosure preferably perform reduction under the above conditions to ensure that the active metal oxide formed during the deposition is reduced to obtain active metal nanoparticles; when the oxides of the first layer, the interlayer and the surface layer are reducible oxides, such as titanium oxide, they are partially reduced (tested by EELS, the valence state of titanium of the interlayer is lower than the positive tetravalent, indicating that part of it is reduced), but still dominated by oxide components.

The method provided by the present disclosure can adjust the thickness of each interface by regulating the number of cycles of deposition periods of various components, and obtain nanometer-sized deposited particles through a deposition process, thereby being able to prepare a multi-sandwich composite catalyst with a clear structure and an adjustable nano-space distance. The multi-sandwich composite catalyst realizes the gradient regulation of different functional centers (catalytically active metals) at the nanometer scale, which is beneficial to obtain a high-performance tandem reaction catalyst suitable for different reaction characteristics, adjustable functional center combination and spatial distance.

Embodiments of the present disclosure provide a multi-sandwich composite catalyst prepared by the preparation method described in the above technical solution, which comprises, in order from the inside to the outside, a first oxide layer, a first active metal layer, an oxide interlayer, and a second active metal layer and a surface oxide layer; the metals in the first active metal layer and the second active metal layer are different kinds of active metals.

The multi-sandwich composite catalyst of the present disclosure comprises, in order from the inside to the outside, a first oxide layer, a first active metal layer, an oxide interlayer, a second active metal layer and a surface oxide layer; the thickness of the first oxide layer is preferably 0.5-20 nm, more preferably 1-15 nm; the thickness of the first active metal layer is preferably 0.5-6 nm, more preferably 1-4 nm; and the thickness of the oxide interlayer is preferably no more than 10 nm, more preferably 0.1-8 nm, most preferably 0.5-5 nm; the thickness of the second active metal layer is preferably 0.5-6 nm, more preferably 1-5 nm, and the thickness of the surface oxide layer is preferably 0.5-20 nm, and more preferably 1-15 nm.

In some embodiments of the present disclosure, in the preparation process, when the carrier is carbon nanotubes or carbon nanofibers, the carrier is converted into a gas when calcined, and the obtained multi-sandwich composite catalyst is a hollow structure; when the carrier is not a carbon nanotube or carbon nanofiber, a multi-sandwich composite catalyst having a hollow structure can still be obtained by the dissolution reaction method to remove the carrier; when the carrier is a porous material, the obtained catalyst is a non-hollow structure, and the active metal exists on the surface of the pore wall to form a porous multi-sandwich composite structure.

In some embodiments of the present disclosure, the metal component in the two active metal layers of the multi-sandwich composite catalyst is preferably determined according to the catalyst required for the tandem reaction, as follows: for the decomposition of the hydrazine hydrate to produce hydrogen and the nitrobenzene hydrogenation reaction, the first active metal layer is preferably a Ni layer, and the second active metal layer is preferably a Pt layer; further, the oxide layer is preferably one or more selected from the group of titanium oxide, aluminum oxide, zinc oxide, gallium oxide and zirconia; for the phenylacetylene hydrogenation reaction and the styrene hydroformylation reaction, the first active metal layer is preferably Pd, and the second active metal layer is preferably Rh; further, the oxide layer is preferably aluminum oxide; for the carbon dioxide hydrogenation reaction, the first active metal layer is preferably Pt, and the second active metal layer is preferably Co; further, the component of the oxide layer is preferably one or more selected from the group of titanium oxide, cerium oxide, zirconia, silicon oxide and aluminum oxide; for the carbon monoxide hydrogenation reaction, the first active metal layer is preferably Cu, and the second active metal layer is preferably Fe; further, the component of the oxide layer is preferably one or more selected from the group of titanium oxide, cerium oxide, zirconia, silicon oxide and aluminum oxide.

In some embodiments of the present disclosure, the multi-sandwich composite catalyst preferably comprises a $TiO_2$/Ni/$TiO_2$/Pt/$TiO_2$ composite catalyst, a $ZrO_2$/Ni/$ZrO_2$/Pt/$ZrO_2$ composite catalyst, a $TiO_2$/Ni/ZnO/Pt/$TiO_2$ composite catalyst, a $TiO_2$/Ni/$Al_2O_3$/Pt/$TiO_2$ composite catalyst, a $TiO_2$/Ni/$Ga_2O_3$/Pt/$TiO_2$ composite catalyst, an $Al_2O_3$/Pd/$Al_2O_3$/Rh/$Al_2O_3$ composite catalyst, a $CeO_2$/Pt/$Al_2O_3$/Co/$SiO_2$ composite catalyst, an $Al_2O_3$/ZnO/Cu/$Al_2O_3$/Fe/$Al_2O_3$ or a $TiO_2$/Cu/$Ga_2O_3$/Fe/$TiO_2$ composite catalyst.

The methods described herein provide the use of the multi-sandwich composite catalyst described in the above technical solution in the tandem catalytic reaction. In the present disclosure, the tandem catalytic reaction is preferably a reaction of several types mentioned in the multi-sandwich composite catalyst described in the above technical solution, and the corresponding relationship between the tandem catalytic reaction and the catalyst used is as described above and will not be repeated here. In the present disclosure, when the tandem catalytic reaction is carried out, the mass ratio of the multi-sandwich composite catalyst to the substrate is preferably 1:10-100.

In order to further illustrate various embodiments of the present disclosure, a multi-sandwich composite catalyst provided by the present disclosure and its preparation method and application are described in detail below with reference to the accompanying drawings and embodiments, but they are not to be construed as limiting the scope of the invention.

Example 1

Figure 1:
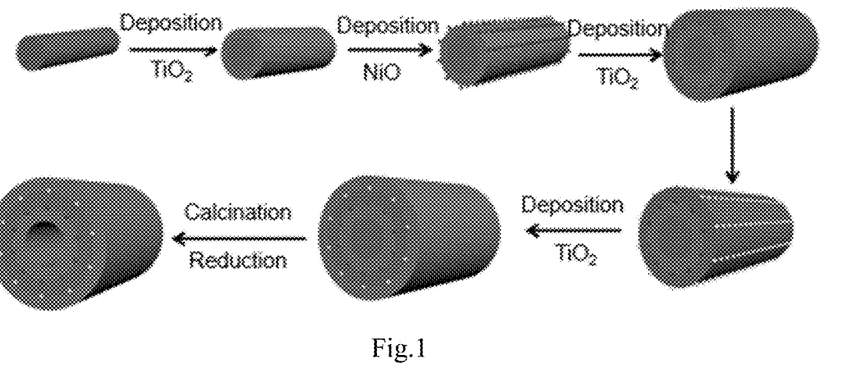
FIG. 1 is a schematic flow chart of preparing $TiO_2/Ni/TiO_2/Pt/TiO_2$ by atomic layer deposition according to the present disclosure.

Preparation and catalytic performance test of $TiO_2$/Ni/$TiO_2$/Pt/$TiO_2$, prepare the catalyst according to the schematic flow chart shown in FIG. 1:

(a) Preparation of CNCs/$TiO_2$:

2 g of carbon nanofibers (150 nm in diameter and 20 μm in length) were mixed with 50 g of a dispersant (anhydrous ethanol), and the obtained carbon nanofiber dispersion was applied onto a glass sheet at a coating amount of 2 g/m$^2$, then removed the solvent to get the template.

The glass sheet coated with carbon nanofibers was placed in an ALD reaction chamber, the reaction temperature of the ALD chamber was 180° C., the temperature of the precursor titanium isopropoxide was 80° C., the temperature of water was 25° C., and the flow rate of nitrogen was 50 sccm. Firstly, the titanium isopropoxide vapor pulse entered into the ALD chamber with a pulse time of 1 s, a diffusion time of 8 s, and a purge time of 20 s; then the water vapor pulse entered into the ALD chamber with a pulse time of 0.1 s, a diffusion time of 8 s and a purge time of 25 s, thereby completing an ALD cycle. The CNCs/$TiO_2$ was obtained by repeating 300 cycles.

(b) Preparation of CNCs/$TiO_2$/NiO:

The above-mentioned glass sheet loaded with CNCs/$TiO_2$ was placed in an ALD reaction chamber, the reaction temperature of the ALD chamber was 295° C., the temperature of the precursor nickelocene was 70° C., and the flow rate of nitrogen was 50 sccm. Firstly, the nickelocene vapor pulse entered into the ALD chamber with a pulse time of 7 s, a diffusion time of 10 s, and a purge time of 25 s; then the ozone pulse entered into the ALD chamber with a pulse time of 1 s, a diffusion time of 10 s, and a purge time of 25 s, thereby completing an ALD cycle. The CNCs/$TiO_2$/NiO was obtained by repeating multiple cycles (100, 300, 500).

(c) Preparation of CNCs/$TiO_2$/NiO/$TiO_2$:

The above-mentioned glass sheet loaded with CNCs/$TiO_2$/NiO was placed in an ALD reaction chamber for $TiO_2$ deposition, the deposition parameters were the same as those in (a), and a certain period of $TiO_2$ was deposited to obtain CNCs/$TiO_2$/NiO/$TiO_2$. By controlling the number of deposition cycles (0, 10, 20, 30, 50, 100) of $TiO_2$ in this process, the distance between Ni and Pt supported by the tandem catalyst can be precisely regulated.

(d) Preparation of CNCs/$TiO_2$/NiO/$TiO_2$/Pt oxide:

The above-mentioned glass sheet loaded with CNCs/$TiO_2$/NiO/$TiO_2$ was placed in an ALD reaction chamber, the reaction temperature of the ALD chamber was 250° C., and the temperature of the precursor trimethylmethylcyclopentadiene platinum was 75° C., the flow rate of nitrogen was 50 sccm. Firstly, the trimethylmethylcyclopentadiene platinum vapor pulse entered into the ALD chamber with a pulse time of 0.5 s, a diffusion time of 10 s, and a purge time of 25 s. Then the ozone pulse entered the ALD chamber with a pulse time of 0.5 s, a diffusion time of 10 s and a purge time of 25 s, thereby completing an ALD cycle. The CNCs/$TiO_2$/NiO/$TiO_2$/Pt oxide was obtained by repeating 20 cycles.

(e) Preparation of CNCs/TiO$_2$/NiO/TiO$_2$/Pt oxide/TiO$_2$:

The above-mentioned glass sheet loaded with CNCs/TiO$_2$/NiO/TiO$_2$/Pt was placed in an ALD reaction chamber for TiO$_2$ deposition. The deposition parameters were the same as those in (a), and the CNCs/TiO$_2$/NiO/TiO$_2$/Pt/TiO$_2$ was obtained by repeating 300 cycles.

(f) The glass sheet loaded with the above CNCs/TiO$_2$/NiO/TiO$_2$/Pt/TiO$_2$ was calcined and reduced to obtain a porous TiO$_2$/Ni/TiO$_2$/Pt/TiO$_2$ catalyst having a specific active site distance. The calcination temperature was 450° C., the heating rate was 5° C./min, the calcination time was 90 min; the reduction atmosphere was 5% H$_2$/Ar mixture gas, the reduction temperature was 380° C., the heating rate was 5° C./min, the reduction time was 120 min.

Figure 2:
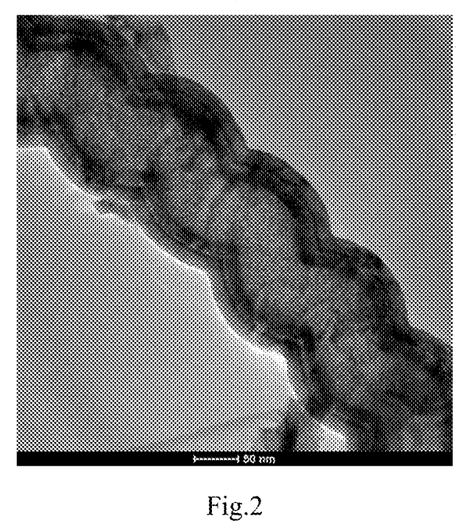
FIG. 2 is a transmission electron micrograph of $300TiO_2/300Ni/10TiO_2/20Pt/300TiO_2$ obtained in Example 1 of the present disclosure.

The obtained catalyst was characterized by a transmission electron microscope (catalyst composition: 300TiO$_2$/300Ni/10TiO$_2$/20Pt/300TiO$_2$), and the results are shown in FIG. 2, as shown in FIG. 2, the obtained catalyst has a clear five-sandwich structure.

(g) Catalytic performance test of 300TiO$_2$/500Ni/(0, 10, 20, 30, 50, 100) TiO$_2$/20Pt/300TiO$_2$.

The decomposition of hydrazine hydrate to produce hydrogen and hydrogenation of nitrobenzene was used as probe reactions. 10 mg of the above catalyst, 800 mg of hydrazine hydrate (85% by mass) and 200 mg of nitrobenzene were placed into the autoclave, and the air in the autoclave was replaced with argon gas to eliminate the interference of air on the reaction, the reaction temperature was 30° C., the magnetic stirring rate was 700 rpm, and the reaction time was 2 h. The catalytic performance is shown in Table 1 below;

Catalytic performance of the catalyst 300TiO$_2$/100Ni/(0, 10, 20, 30, 50, 100) TiO$_2$/20Pt/300TiO$_2$ and the catalyst 300TiO$_2$/300Ni/(0, 10, 20, 30, 50, 100) TiO$_2$/20Pt/300TiO$_2$ were tested according to the same conditions. The test results are listed in Table 1.

TABLE 1

Catalytic performance of the catalyst obtained in Example 1

| Catalyst | Conversion (%) | Selectivity (%) |
| --- | --- | --- |
| 300TiO$_2$/500Ni/0TiO$_2$/20Pt/300TiO$_2$ | 26.30 | >99 |
| 300TiO$_2$/500Ni/10TiO$_2$/20Pt/300TiO$_2$ | 55.84 | >99 |
| 300TiO$_2$/500Ni/20TiO$_2$/20Pt/300TiO$_2$ | 66.21 | >99 |
| 300TiO$_2$/500Ni/30TiO$_2$/20Pt/300TiO$_2$ | 79.52 | >99 |
| 300TiO$_2$/500Ni/50TiO$_2$/20Pt/300TiO$_2$ | 35.57 | >99 |
| 300TiO$_2$/500Ni/100TiO$_2$/20Pt/300TiO$_2$ | 30.22 | >99 |
| 300TiO$_2$/100Ni/0TiO$_2$/20Pt/300TiO$_2$ | 10.02 | >99 |
| 300TiO$_2$/100Ni/10TiO$_2$/20Pt/300TiO$_2$ | 19.53 | >99 |
| 300TiO$_2$/100Ni/20TiO$_2$/20Pt/300TiO$_2$ | 16.44 | >99 |
| 300TiO$_2$/100Ni/30TiO$_2$/20Pt/300TiO$_2$ | 12.17 | >99 |
| 300TiO$_2$/100Ni/50TiO$_2$/20Pt/300TiO$_2$ | 10.76 | >99 |
| 300TiO$_2$/100Ni/100TiO$_2$/20Pt/300TiO$_2$ | 7.85 | >99 |
| 300TiO$_2$/300Ni/0TiO$_2$/20Pt/300TiO$_2$ | 16.60 | >99 |
| 300TiO$_2$/300Ni/10TiO$_2$/20Pt/300TiO$_2$ | 25.31 | >99 |
| 300TiO$_2$/300Ni/20TiO$_2$/20Pt/300TiO$_2$ | 20.10 | >99 |
| 300TiO$_2$/300Ni/30TiO$_2$/20Pt/300TiO$_2$ | 18.19 | >99 |
| 300TiO$_2$/300Ni/50TiO$_2$/20Pt/300TiO$_2$ | 13.09 | >99 |
| 300TiO$_2$/300Ni/100TiO$_2$/20Pt/300TiO$_2$ | 9.98 | >99 |

It can be seen from the data in Table 1 that the catalytic activity and the distance between Pt and Ni exhibit a volcanic relationship that increases first and then decreases. When nickel is 500 cycles and the distance between Ni and Pt is 30 cycles of TiO$_2$ thickness, the catalyst has the highest activity in the tandem reaction, the conversion rate reaches 79.52%, and the selectivity of the target product aniline is over 99%.

Example 2

The test was carried out in the same manner as in Example 1, except that the oxide interlayer was changed to ZnO to prepare 300TiO$_2$/500Ni/(0, 10, 20, 30, 50, 100) ZnO/20Pt/300TiO$_2$. The catalytic performance test was carried out. The results show that the conversion and the distance between the active sites exhibit a volcanic relationship. When the number of cycles of the interlayer oxide (ZnO) deposition is 30, the conversion of nitrobenzene is the highest, reaching 60.10%, lower than that of the catalyst with TiO$_2$ as the oxide interlayer, but higher than that of the catalyst without an oxide interlayer, indicating that the oxide interlayer can improve the catalytic activity of the catalyst; but compared with ZnO, the TiO$_2$ interlayer is more favorable for the mass transfer of the reactants, and therefore, the catalytic activity of the catalyst is more advantageous.

Example 3

The test was carried out in the same manner as in Example 1, except that the oxide interlayer was Al$_2$O$_3$, to prepare 300TiO$_2$/500Ni/(0, 10, 20, 30, 50, 100) Al$_2$O$_3$/20Pt/300TiO$_2$. The catalytic performance test was carried out. The results show that the conversion and the distance between the active sites exhibit a volcanic relationship. When the number of cycles of the oxide interlayer (Al$_2$O$_3$) is 20, the conversion rate of nitrobenzene is the highest, reaching 44.12%, lower than that of the catalyst with TiO$_2$ as the interlayer, but higher than that of the catalyst without a interlayer.

Example 4

The test was carried out in the same manner as in Example 1, except that the oxide interlayer was Ga$_2$O$_3$, to prepare 300TiO$_2$/500Ni/(0, 10, 20, 30, 50, 100) Ga$_2$O$_3$/20Pt/300TiO$_2$. The catalytic performance test was carried out. The results show that the conversion and the distance between the active sites exhibit a volcanic relationship. When the number of cycles of the oxide interlayer (Ga$_2$O$_3$) is 40, the conversion rate of nitrobenzene is the highest, reaching 30.86%, lower than that of the catalyst with TiO$_2$ as the interlayer, but higher than that of the catalyst without an interlayer.

Example 5

Preparation and catalytic performance test of ZrO$_2$/Ni/ZrO$_2$/Pt/ZrO$_2$ (a) Preparation of CNCs/ZrO$_2$:

A template was prepared in the same manner as in Example 1, and a glass sheet coated with carbon nanofibers was placed in an ALD reaction chamber. The reaction temperature of the ALD chamber was 180° C., the temperature of the precursor zirconium tert-butoxide was 80° C., and the temperature of water was 25° C. The flow rate of nitrogen was 50 sccm. Firstly, the zirconium tert-butoxide vapor pulse entered the ALD chamber with a pulse time of 1 s, a diffusion time of 8 s, and a purge time of 20 s; then the water vapor pulse entered the ALD chamber with a pulse time of 0.1 s, a diffusion time of 8 s, and a purge time of 25 s, thereby completing an ALD cycle. The CNCs/ZrO$_2$ was obtained by repeating 300 cycles.

(b) Preparation of CNCs/ZrO$_2$/NiO:

The above-mentioned glass sheet loaded with CNCs/ZrO$_2$ was placed in an ALD reaction chamber, the reaction temperature of the ALD chamber was 295° C., the temperature of the precursor nickelocene was 70° C., and the flow rate of nitrogen was 50 sccm. Firstly, the nickelocene vapor pulse entered the ALD chamber with a pulse time of 7 s, a diffusion time of 10 s, and a purge time of 25 s; then the ozone pulse entered the ALD chamber with a pulse time of 1 s, a diffusion time of 10 s, and a purge time of 25 s, thus completing an ALD cycle. The CNCs/$ZrO_2$/NiO was obtained by repeating multiple cycles (100, 300, 500).

(c) Preparation of CNCs/$ZrO_2$/NiO/$ZrO_2$:

The above-mentioned glass sheet loaded with CNCs/$ZrO_2$/NiO was placed in an ALD reaction chamber for $ZrO_2$ deposition. The deposition parameters were the same as those in (a), and a certain cycle of $ZrO_2$ was deposited to obtain CNCs/$ZrO_2$/NiO/$ZrO_2$. By controlling the number of deposition cycles (0, 10, 20, 30, 50, 100) of $ZrO_2$ in this process, the distance between Ni and Pt supported by the tandem catalyst can be precisely regulated.

(d) Preparation of CNCs/$ZrO_2$/NiO/$ZrO_2$/Pt oxide:

The above-mentioned glass sheet loaded with CNCs/$ZrO_2$/NiO/$ZrO_2$ was placed in an ALD reaction chamber, the reaction temperature of the ALD chamber was 250° C., and the temperature of the precursor trimethylmethylcyclopentadiene platinum was 75° C., the flow rate of nitrogen was 50 sccm. Firstly, the trimethylmethylcyclopentadiene platinum vapor pulse entered the ALD chamber with a pulse time of 0.5 s, a diffusion time of 10 s, and a purge time of 25 s; then the ozone pulse entered the ALD chamber with a pulse time of 0.5 s, a diffusion time of 10 s and a purge time of 25 s, thereby completing an ALD cycle. The CNCs/$ZrO_2$/NiO/$ZrO_2$/Pt oxide was obtained by repeating 20 cycles.

(e) Preparation of CNCs/$ZrO_2$/NiO/$ZrO_2$/Pt oxide/$ZrO_2$:

The glass sheet loaded with the above-mentioned CNCs/$ZrO_2$/NiO/$ZrO_2$/Pt oxide was placed in the ALD reaction chamber for $ZrO_2$ deposition. The deposition parameters were the same as those in (a), and the CNCs/$ZrO_2$/NiO/$ZrO_2$/Pt oxide/$ZrO_2$ was obtained by repeating 300 cycles of $ZrO_2$ deposition.

(f) The above-mentioned CNCs/$ZrO_2$/NiO/$ZrO_2$/Pt oxide/$ZrO_2$ was calcined and reduced to obtain a porous $ZrO_2$/Ni/$ZrO_2$/Pt/$ZrO_2$ catalyst having a specific active site distance. The calcination temperature was 450° C., the heating rate was 5° C./min, the calcination time was 90 min, the reduction atmosphere was 5% $H_2$/Ar mixture gas, the reduction temperature was 380° C., the heating rate was 5° C./min, the reduction time was 120 min.

(g) Catalytic performance test of 300$ZrO_2$/500Ni/(0, 10, 20, 30, 50, 100) $ZrO_2$/20Pt/300$ZrO_2$.

The decomposition reaction of hydrazine hydrate to produce hydrogen and the hydrogenation of nitrobenzene were used as probe reactions, and 10 mg of the above catalyst, 800 mg of hydrazine hydrate (85%) and 200 mg of nitrobenzene were placed into the autoclave, and the air in the reaction vessel was replaced with argon gas to eliminate the interference of air on the reaction, the reaction temperature was 30° C., the magnetic stirring speed was 700 rpm, and the reaction time was 2 h. The test results are shown in Table 2.

TABLE 2

Catalytic performance of the catalyst obtained in Example 5

| Catalyst | Conversion (%) | Selectivity (%) |
|---|---|---|
| 300$ZrO_2$/300Ni/0$ZrO_2$/20Pt/300$ZrO_2$ | 12.35 | >99 |
| 300$ZrO_2$/300Ni/10$ZrO_2$/20Pt/300$ZrO_2$ | 22.16 | >99 |

TABLE 2-continued

Catalytic performance of the catalyst obtained in Example 5

| Catalyst | Conversion (%) | Selectivity (%) |
|---|---|---|
| 300$ZrO_2$/300Ni/20$ZrO_2$/20Pt/300$ZrO_2$ | 18.46 | >99 |
| 300$ZrO_2$/300Ni/30$ZrO_2$/20Pt/300$ZrO_2$ | 15.54 | >99 |
| 300$ZrO_2$/300Ni/50$ZrO_2$/20Pt/300$ZrO_2$ | 11.28 | >99 |
| 300$ZrO_2$/300Ni/100$ZrO_2$/20Pt/300$ZrO_2$ | 7.71 | >99 |
| 300$ZrO_2$/100Ni/0$ZrO_2$/20Pt/300$ZrO_2$ | 8.59 | >99 |
| 300$ZrO_2$/100Ni/10$ZrO_2$/20Pt/300$ZrO_2$ | 15.96 | >99 |
| 300$ZrO_2$/100Ni/20$ZrO_2$/20Pt/300$ZrO_2$ | 12.39 | >99 |
| 300$ZrO_2$/100Ni/30$ZrO_2$/20Pt/300$ZrO_2$ | 10.86 | >99 |
| 300$ZrO_2$/100Ni/50$ZrO_2$/20Pt/300$ZrO_2$ | 7.94 | >99 |
| 300$ZrO_2$/100Ni/100$ZrO_2$/20Pt/300$ZrO_2$ | 5.64 | >99 |
| 300$ZrO_2$/500Ni/0$ZrO_2$/20Pt/300$ZrO_2$ | 26.30 | >99 |
| 300$ZrO_2$/500Ni/10$ZrO_2$/20Pt/300$ZrO_2$ | 45.36 | >99 |
| 300$ZrO_2$/500Ni/20$ZrO_2$/20Pt/300$ZrO_2$ | 71.63 | >99 |
| 300$ZrO_2$/500Ni/30$ZrO_2$/20Pt/300$ZrO_2$ | 66.24 | >99 |
| 300$ZrO_2$/500Ni/50$ZrO_2$/20Pt/300$ZrO_2$ | 50.87 | >99 |
| 300$ZrO_2$/500Ni/100$ZrO_2$/20Pt/300$ZrO_2$ | 39.62 | >99 |

It can be seen from the test results in Table 2 that the catalytic activity of the catalyst obtained in this example and the distance between the two active metals exhibit a volcanic relationship, the nitrobenzene conversion of the 300$ZrO_2$/300Ni/20$ZrO_2$/20Pt/300$ZrO_2$ catalyst is the highest, reaching 71.63%, and the aniline selectivity is over 99%.

Example 6

The test was carried out in the same manner as in Example 1, except that the hydrogenation substrate was changed to 4-nitrostyrene to prepare 300$TiO_2$/500Ni/(0, 10, 20, 30, 50, 100) $TiO_2$/20Pt/300$TiO_2$. The catalytic performance test conditions were the same as those in Example 1. The test results show that when the catalytic reaction types are the same, but the substrates are different, the structure of the catalyst needs to be adjusted, and the method provided by the present technical solution can precisely regulate the distance between the two active metal centers, therefore, it is possible to prepare catalysts that meet different substrates and even different tandem reactions.

Example 7

Preparation and Catalytic Performance Test of $Al_2O_3$/Pd/$Al_2O_3$/Rh/$Al_2O_3$ (a) Preparation of CNCs/$Al_2O_3$:

A template was provided in the manner of Example 1, and a glass sheet coated with carbon nanofibers was placed in an ALD reaction chamber. The reaction temperature of the ALD chamber was 180° C., the temperature of the precursor trimethylaluminum was 25° C., and the temperature of water was 25° C. The flow rate of nitrogen was 50 sccm. Firstly, the trimethylaluminum vapor pulse entered the ALD chamber with a pulse time of 0.1 s, a diffusion time of 8 s, and a purge time of 20 s; then the water vapor pulse entered the ALD chamber with a pulse time of 0.1 s, a diffusion time of 8 s, and a purge time of 25 s, thereby completing an ALD cycle. The CNCs/$Al_2O_3$ was obtained by repeating 300 cycles.

(b) Preparation of CNCs/$Al_2O_3$/Pd oxide:

The above-mentioned glass sheet loaded with CNCs/$Al_2O_3$ was placed in an ALD reaction chamber, the reaction temperature of the ALD chamber was 180° C., the temperature of the precursor hexafluoroacetylacetonate palladium was 60° C., and the flow rate of nitrogen was 50 sccm. Firstly, the hexafluoroacetylacetonate palladium vapor pulse entered the ALD chamber with a pulse time of 0.5 s, a diffusion time of 8 s, and a purge time of 20 s. Then the formalin pulse entered the ALD chamber with a pulse time of 0.5 s, a diffusion time of 8 s, and a purge time of 20 s, thereby completing an ALD cycle. The CNCs/Al$_2$O$_3$/Pd oxide was obtained by repeating 10 cycles.

(c) Preparation of CNCs/Al$_2$O$_3$/Pd oxide/Al$_2$O$_3$:

The above-mentioned glass sheet loaded with CNCs/Al$_2$O$_3$/Pd oxide was placed in an ALD reaction chamber for Al$_2$O$_3$ deposition. The deposition parameters were the same as those in (a), and a certain cycle of Al$_2$O$_3$ was deposited to obtain CNCs/Al$_2$O$_3$/Pd/Al$_2$O$_3$. By controlling the number of deposition cycles (0, 10, 20, 30, 50, 100) of Al$_2$O$_3$ in this process, the distance between Pd and Rh supported by the tandem catalyst can be precisely regulated.

(d) Preparation of CNCs/Al$_2$O$_3$/Pd Oxide/Al$_2$O$_3$/Rh oxide:

The above-mentioned glass sheet loaded with CNCs/Al$_2$O$_3$/Pd oxide/Al$_2$O$_3$ was placed in the ALD reaction chamber, the reaction temperature of the ALD chamber was 250° C., and the temperature of the precursor triacetylacetone rhodium was 75° C. and the flow rate of nitrogen was 50 sccm. Firstly, the triacetylacetone rhodium vapor pulse entered the ALD chamber with a pulse time of 0.5 s, a diffusion time of 10 s, and a purge time of 25 s; then the ozone pulse entered the ALD chamber with a pulse time of 0.5 s, a diffusion time of 10 s, and a purge time of 25 s, thereby completing an ALD cycle. The CNCs/Al$_2$O$_3$/Pd oxide/Al$_2$O$_3$/Rh oxide was obtained by repeating 20 cycles.

(e) Preparation of CNCs/Al$_2$O$_3$/Pd oxide/Al$_2$O$_3$/Rh oxide/Al$_2$O$_3$:

The above-mentioned glass sheet loaded with CNCs/Al$_2$O$_3$/Pd oxide/Al$_2$O$_3$/Rh oxide was placed in an ALD reaction chamber for Al$_2$O$_3$ deposition. The deposition parameters were the same as those in (a), and CNCs/Al$_2$O$_3$/Pd/Al$_2$O$_3$/Rh/Al$_2$O$_3$ was obtained by repeating 300 cycles of Al$_2$O$_3$ deposition.

(f) The above-mentioned CNCs/Al$_2$O$_3$/Pd oxide/Al$_2$O$_3$/Rh oxide/Al$_2$O$_3$ was calcined and reduced to obtain a porous Al$_2$O$_3$/Pd/Al$_2$O$_3$/16/Al$_2$O$_3$ catalyst with a specific active site distance. The calcination temperature was 450° C., the heating rate was 5° C./min, the calcination time was 90 min, the reduction atmosphere was 5% H$_2$/Ar mixture gas, the reduction temperature was 450° C., the heating rate was 5° C./min, the reduction time was 120 min.

(g) Catalytic performance test of Al$_2$O$_3$/Pd/Al$_2$O$_3$/Rh/Al$_2$O$_3$.

The selective hydrogenation of phenylacetylene and the hydroformylation of styrene were used as probe reactions, 10 mg of the above catalyst, 100 mg of phenylacetylene were placed into the autoclave, the solvent dichloromethane was 10 mL, and the air in the autoclave was replaced with hydrogen to eliminate the interference of air on the reaction, the CO pressure was 1.0 MPa, the H$_2$ pressure was 3.0 MPa, the reaction temperature was 80° C., the magnetic stirring speed was 700 rpm, and the reaction time was 4 h. The catalytic performance is shown in Table 3.

TABLE 3

Catalytic performance of the catalyst obtained in Example 7

| Catalyst | Conversion (%) | Selectivity (%) |
|---|---|---|
| 300Al$_2$O$_3$/10Pd/0Al$_2$O$_3$/20Rh/300Al$_2$O$_3$ | 50.10 | 92 |
| 300Al$_2$O$_3$/10Pd/10Al$_2$O$_3$/20Rh/300Al$_2$O$_3$ | 80.12 | 92 |
| 300Al$_2$O$_3$/10Pd/20Al$_2$O$_3$/20Rh/300Al$_2$O$_3$ | 75.31 | 92 |
| 300Al$_2$O$_3$/10Pd/30Al$_2$O$_3$/20Rh/300Al$_2$O$_3$ | 70.13 | 92 |
| 300Al$_2$O$_3$/10Pd/50Al$_2$O$_3$/20Rh/300Al$_2$O$_3$ | 53.47 | 92 |
| 300Al$_2$O$_3$/10Pd/100Al$_2$O$_3$/20Rh/300Al$_2$O$_3$ | 42.56 | 92 |

It can be seen from the test results in Table 3 that the catalytic activity of the catalyst and the distance between the two active metals exhibit a volcanic relationship, when the number of cycles of the oxide interlayer deposition is 10, the phenylacetylene conversion of the obtained composite catalyst (300Al$_2$O$_3$/10Pd/10Al$_2$O$_3$/20Rh/300Al$_2$O$_3$) is the highest, reaching 80.12%, and the phenylpropanol selectivity is over 90%.

Example 8

Preparation and Catalytic Performance Testing of CeO$_2$/Pt/Al$_2$O$_3$/Co/SiO$_2$.

(a) Preparation of CNCs/CeO$_2$:

A template was prepared in the same manner as in Example 1, and a glass sheet coated with carbon nanofibers was placed in an ALD reaction chamber. The reaction temperature of the ALD chamber was 250° C., and the temperature of the precursor tris(isopropylcyclopentadiene) cerium was 80° C., the temperature of water was 25° C., the flow rate of nitrogen was 50 sccm. Firstly, the tris(isopropylcyclopentadiene) cerium vapor pulse entered the ALD chamber with a pulse time of 1 s, a diffusion time of 8 s, and a purge time of 20 s; then the water vapor pulse entered the ALD chamber with a pulse time of 0.1 s, a diffusion time of 8 s and a purge time of 25 s, thereby completing an ALD cycle. The CNCs/CeO$_2$ was obtained by repeating 300 cycles.

(b) Preparation of CNCs/CeO$_2$/Pt oxides:

The above-mentioned glass sheet loaded with CNCs/CeO$_2$ was placed in an ALD reaction chamber, the reaction temperature of the ALD chamber was 250° C., the temperature of the precursor trimethylmethylcyclopentadiene platinum was 75° C., and the flow rate of nitrogen was 50 sccm. Firstly, the trimethylmethylcyclopentadiene platinum vapor pulse entered the ALD chamber with a pulse time of 0.5 s, a diffusion time of 10 s, and a purge time of 25 s; then the ozone pulse entered the ALD chamber with a pulse time of 0.5 s, a diffusion time of 10 s and the purge time of 25 s, thereby completing an ALD cycle. The CNCs/CeO$_2$/Pt oxide was obtained by repeating 10 cycles.

(c) Preparation of CNCs/CeO$_2$/Pt oxide/Al$_2$O$_3$:

The above-mentioned glass sheet loaded with CNCs/CeO$_2$/Pt oxide was placed in an ALD reaction chamber for Al$_2$O$_3$ deposition, the reaction temperature of the ALD chamber was 180° C., and the temperature of the precursor trimethylaluminum was 25° C., the temperature of water was 25° C., and the flow rate of nitrogen was 50 sccm. Firstly, the trimethylaluminum vapor pulse entered the ALD chamber with a pulse time of 0.1 s, a diffusion time of 8 s, and a purge time of 20 s; then the water vapor pulse entered the ALD chamber with a pulse time of 0.1 s, a diffusion time of 8 s, and a purge time of 25 s, thereby completing an ALD cycle. A certain cycle of Al$_2$O$_3$ was deposited to obtain CNCs/CeO$_2$/Pt/Al$_2$O$_3$. By controlling the number of deposition cycles (0, 10, 20, 30, 50, 100) of Al$_2$O$_3$ in this process, the distance between Pt and Co supported by the tandem catalyst can be precisely regulated.

(d) Preparation of CNCs/CeO$_2$/Pt oxide/Al$_2$O$_3$/Co oxide:

The above-mentioned glass sheet loaded with CNCs/CeO$_2$/Pt oxide/Al$_2$O$_3$ was placed in the ALD reaction chamber, the reaction temperature of the ALD chamber was 250° C., and the temperature of the precursor cobaltocene was 75° C., the flow rate of nitrogen was 50 sccm. Firstly, the cobaltocene vapor pulse entered the ALD chamber with a pulse time of 0.5 s, a diffusion time of 10 s, and a purge time of 25 s; then the ozone pulse entered the ALD chamber with a pulse time of 0.5 s, a diffusion time of 10 s, and a purge time of 25 s, thereby completing an ALD cycle. The CNCs/CeO$_2$/Pt oxide/Al$_2$O$_3$/Co oxide was obtained by repeating 20 cycles.

(e) Preparation of CNCs/CeO$_2$/Pt/Al$_2$O$_3$/Co/SiO$_2$:

The above-mentioned glass sheet loaded with CNCs/CeO$_2$/Pt oxide/Al$_2$O$_3$/Co oxide was placed in an ALD reaction chamber for SiO$_2$ deposition, and the reaction temperature of the ALD chamber was 250° C. The temperature of the precursor tris(dimethylamino)silane was 40° C. and the flow rate of nitrogen was 50 sccm. Firstly, the tris(dimethylamino)silane vapor pulse entered the ALD chamber with a pulse time of 0.5 s, a diffusion time of 10 s, and a purge time of 25 s; then the ozone pulse entered the ALD chamber with a pulse time of 0.5 s, a diffusion time of 10 s, and a purge time of 25 s, thereby completing an ALD cycle. CNCs/CeO$_2$/Pt oxide/Al$_2$O$_3$/Co oxide/SiO$_2$ was obtained by repeating 300 cycles of SiO$_2$ deposition.

(f) The above-mentioned CNCs/CeO$_2$/Pt oxide/Al$_2$O$_3$/Co oxide/SiO$_2$ was calcined and reduced to obtain a porous CeO$_2$/Pt/Al$_2$O$_3$/Co/SiO$_2$ catalyst with a specific active site distance. The calcination temperature was 450° C., the heating rate was 5° C./min, the calcination time was 90 min. The reduction atmosphere was 5% H$_2$/Ar mixed gas, the reduction temperature was 500° C., the heating rate was 5° C./min, the reduction time was 120 min.

(g) Catalytic performance test of CeO$_2$/Pt/Al$_2$O$_3$/Co/SiO$_2$.

The carbon dioxide hydrogenation reaction was used as a probe reaction. In the fixed bed reactor, 10 mg of the above catalyst was taken, the pressure of CO$_2$ was 1.0 MPa, the pressure of H$_2$ was 3.0 MPa, and the reaction temperature was 250° C. The results show that the selectivity of product C$_2$-C$_4$ alkane and the distance between the two active metal layers exhibit volcanic relationship, the C$_2$-C$_4$ alkane selectivity of CeO$_2$/Pt/30Al$_2$O$_3$/Co/SiO$_2$ catalyst is the highest, reaching 60.12%.

Example 9

Preparation and catalytic performance of TiO$_2$/Ni/TiO$_2$/Pt/TiO$_2$ using aluminum oxide nanowires as the template.

(a) Preparation of Al$_2$O$_3$/TiO$_2$:

2 g of aluminum oxide nanowires were mixed with 50 g of absolute ethanol, and the resulting dispersion was applied to a glass sheet at a coating amount of 2 g/m$^2$. After removing the solvent, a template was obtained.

The glass sheet coated with the aluminum oxide nanowire was placed in the ALD reaction chamber, the reaction temperature of the ALD chamber was 180° C., the temperature of the precursor titanium isopropoxide was 80° C., the temperature of water was 25° C., and the flow rate of nitrogen was 50 sccm. Firstly, the titanium isopropoxide vapor pulse entered the ALD chamber with a pulse time of 1 s, a diffusion time of 8 s, and a purge time of 20 s; then the water vapor pulse entered the ALD chamber with a pulse time of 0.1 s, a diffusion time of 8 s, and a pulse time of 25 s, thereby completing an ALD cycle. Al$_2$O$_3$/TiO$_2$ was obtained by repeating 300 cycles.

(b) Preparation of Al$_2$O$_3$/TiO$_2$/NiO:

The above-mentioned glass sheet of Al$_2$O$_3$/TiO$_2$ was placed in an ALD reaction chamber, the reaction temperature of the ALD chamber was 295° C., the temperature of the precursor nickelocene was 70° C., and the flow rate of nitrogen was 50 sccm. Firstly, the nickelocene vapor pulse entered the ALD chamber with a pulse time of 7 s, a diffusion time of 10 s, and a purge time of 25 s; then the ozone pulse entered the ALD chamber with a pulse time of 1 s, a diffusion time of 10 s, and a purge time of 25 s, thus completing an ALD cycle. The CNCs/TiO$_2$/NiO was obtained by repeating 300 cycles.

(c) Preparation of Al$_2$O$_3$/TiO$_2$/NiO/TiO$_2$:

The above-mentioned glass sheet loaded with Al$_2$O$_3$/TiO$_2$/NiO was placed in the ALD reaction chamber for TiO$_2$ deposition. The deposition parameters were the same as those in (a), and a certain cycle of TiO$_2$ was deposited to obtain Al$_2$O$_3$/TiO$_2$/NiO/TiO$_2$. By controlling the number of deposition cycles (0, 10, 20, 30, 50, 100) of TiO$_2$ in this process, the distance between Ni and Pt supported by the tandem catalyst can be precisely regulated.

(d) Preparation of Al$_2$O$_3$/TiO$_2$/NiO/TiO$_2$/Pt oxide:

The above-mentioned glass sheet loaded with Al$_2$O$_3$/TiO$_2$/NiO/TiO$_2$ was placed in the ALD reaction chamber, the reaction temperature of the ALD chamber was 250° C., and the temperature of the precursor trimethylmethylcyclopentadiene platinum was 75° C. and the flow rate of nitrogen was 50 sccm. Firstly, the trimethylmethylcyclopentadiene platinum vapor pulse entered the ALD chamber with a pulse time of 0.5 s, a diffusion time of 10 s, and a purge time of 25 s; then the ozone pulse entered the ALD chamber with a pulse time of 0.5 s, a diffusion time of 10 s and a purge time of 25 s, thereby completing an ALD cycle. The CNCs/TiO$_2$/NiO/TiO$_2$/Pt was obtained by repeating 20 cycles.

(e) Preparation of Al$_2$O$_3$/TiO$_2$/NiO/TiO$_2$/Pt oxide/TiO$_2$:

The above-mentioned glass sheet loaded with Al$_2$O$_3$/TiO$_2$/NiO/TiO$_2$/Pt oxide was placed in an ALD reaction chamber for TiO$_2$ deposition, the deposition parameters were the same with those used in (a), and Al$_2$O$_3$/TiO$_2$/NiO/TiO$_2$/Pt/TiO$_2$ was obtained by repeating 300 cycles of TiO$_2$ deposition.

(f) The above Al$_2$O$_3$/TiO$_2$/NiO/TiO$_2$/Pt oxide/TiO$_2$ sample was treated with dilute hydrochloric acid to remove the aluminum oxide nanowire template, and then carried out calcination and reduction treatment, to obtain a porous TiO$_2$/Ni/TiO$_2$/Pt/TiO$_2$ catalyst having a specific active site distance. The calcination temperature was 450° C., the heating rate was 5° C./min, the calcination time was 90 min; the reduction atmosphere was 5% H$_2$/Ar mixture gas, the reduction temperature was 380° C., the heating rate was 5° C./min, the reduction time was 120 min.

(g) Catalytic performance test of 300TiO$_2$/300Ni/ (0, 10, 20, 30, 50, 100) TiO$_2$/20Pt/300TiO$_2$.

Decomposition of hydrazine hydrate to produce hydrogen and hydrogenation of nitrobenzene were used as probe reactions. 10 mg of the above catalyst, 800 mg of hydrazine hydrate (85% by mass) and 200 mg of nitrobenzene were placed into the autoclave, and the air in the autoclave was replaced with argon gas to eliminate the interference of air on the reaction, the reaction temperature was 30° C., the magnetic stirring speed was 700 rpm, and the reaction time was 2 h.

The results show that the catalytic activity and the distance between Pt and Ni exhibit volcanic relationships which increases first and then decreases. When the nickel is 300 cycles, the distance between Ni and Pt is 10 cycles of $TiO_2$, the catalyst in the tandem reaction has the highest activity, the conversion of nitrobenzene is 19.80%, and the selectivity of the target product aniline is over 99%.

Example 10

Preparation and Catalytic Performance Test of $Al_2O_3$/ZnO/Cu/$Al_2O_3$/Fe/$Al_2O_3$ Using Porous Aluminum Oxide Spheres as the Template (a) Preparation of $Al_2O_3$/ZnO:

2 g of porous aluminum oxide spheres were mixed with 50 g of absolute ethanol, and the obtained porous aluminum oxide spheres dispersion was applied to a glass sheet at a coating amount of 2 g/m², which was naturally air-dried to remove the dispersant.

A glass sheet coated with porous aluminum oxide spheres was placed in an ALD reaction chamber. The reaction temperature of the ALD chamber was 180° C., the temperature of the precursor diethyl zinc was 25° C., the temperature of water was 25° C., and the flow rate of nitrogen was 50 sccm. Firstly, the diethyl zinc vapor pulse entered the ALD chamber with a pulse time of 1 s, a diffusion time of 8 s, and a purge time of 20 s; then the water vapor pulse entered the ALD chamber with a pulse time of 0.1 s, a diffusion time of 8 s, and a purge time of 25 s, thereby completing an ALD cycle. $Al_2O_3$/ZnO was obtained by repeating 300 cycles.

(b) Preparation of $Al_2O_3$/ZnO/Cu oxide:

The above-mentioned glass sheet loaded with $Al_2O_3$/ZnO was placed in the ALD reaction chamber, the reaction temperature of the ALD chamber was 250° C., the temperature of the di(tert-butylacetylacetone) copper vapor was 80° C., and the flow rate of nitrogen was 50 sccm. Firstly, the bis(tert-butylacetylacetone) copper vapor pulse entered the ALD chamber with a pulse time of 2 s, a diffusion time of 10 s, and a purge time of 25 s; then the ozone pulse entered the ALD chamber with a pulse time of 1 s, a diffusion time of 10 s, and a purge time of 25 s, thus completing an ALD cycle. $Al_2O_3$/ZnO/Cu oxide was obtained by repeating 50 cycles.

(c) Preparation of $Al_2O_3$/ZnO/Cu oxide/$Al_2O_3$:

The above-mentioned glass sheet loaded with $Al_2O_3$/ZnO/Cu oxide was placed in an ALD reaction chamber for $Al_2O_3$ deposition, and the reaction temperature of the ALD chamber was 180° C., and the temperature of the precursor trimethylaluminum was 25° C., the temperature of water was 25° C., and the flow rate of nitrogen was 50 sccm. Firstly, the trimethylaluminum vapor pulse entered the ALD chamber with a pulse time of 0.1 s, a diffusion time of 8 s, and a purge time of 20 s; then the water vapor pulse entered the ALD chamber with a pulse time of 0.1 s, a diffusion time of 8 s, and a purge time of 25 s, thereby completing an ALD cycle. A certain cycle of $Al_2O_3$ was deposited to obtain $Al_2O_3$/ZnO/Cu/$Al_2O_3$, by controlling the number of cycles (0, 10, 20, 30, 50, 100) of $Al_2O_3$ deposition during this process, the distance between Cu and Fe supported by the tandem catalyst can be precisely regulated.

(d) Preparation of $Al_2O_3$/ZnO/Cu oxide/$Al_2O_3$/Fe oxide:

The above-mentioned glass sheet of $Al_2O_3$/ZnO/Cu oxide/$Al_2O_3$ was placed in the ALD reaction chamber, and the reaction temperature of the ALD chamber was 250° C. The temperature of the precursor ferrocene was 75° C. and the flow rate of nitrogen was 50 sccm. Firstly, the ferrocene vapor pulse entered the ALD chamber, the pulse time was 2 s, the diffusion time was 10 s, the purge time was 25 s; then the ozone pulse entered the ALD chamber, the pulse time was 0.5 s, the diffusion time was 10 s, the purge time was 25 s, thereby completing an ALD cycle. The $Al_2O_3$/ZnO/Cu oxide/$Al_2O_3$/Fe oxide was obtained by repeating 50 cycles.

(e) Preparation of $Al_2O_3$/ZnO/Cu/$Al_2O_3$/Fe/$Al_2O_3$:

The above-mentioned glass sheet loaded with $Al_2O_3$/ZnO/Cu oxide/$Al_2O_3$/Fe oxide was placed in an ALD reaction chamber for $Al_2O_3$ deposition. The deposition parameters were the same as those in (c), and $Al_2O_3$/ZnO/Cu oxide/$Al_2O_3$/Fe oxide/$Al_2O_3$ was obtained by repeating 300 cycles of $Al_2O_3$ deposition.

(f) The above $Al_2O_3$/ZnO/Cu oxide/$Al_2O_3$/Fe oxide/$Al_2O_3$ sample was calcined and reduced, to obtain a porous $Al_2O_3$/ZnO/Cu/$Al_2O_3$/Fe/$Al_2O_3$ catalyst having a specific active site distance. The calcination temperature was 450° C., the heating rate was 5° C./min, the calcination time was 90 min; the reduction atmosphere was 5% $H_2$/Ar mixture gas, the reduction temperature was 400° C., the heating rate was 5° C./min, the reduction time was 120 min.

(g) Catalytic performance test of $Al_2O_3$/ZnO/Cu/(0, 10, 20, 30, 50, 100) $Al_2O_3$/Fe/$Al_2O_3$ The carbon monoxide hydrogenation reaction was used as a probe reaction. In the fixed bed reactor, 10 mg of the above catalyst was taken, the CO pressure was 2.0 MPa, the $H_2$ pressure was 4.0 MPa, the space velocity was 6000 $h^{-1}$, and the reaction temperature was 320° C. The test results are listed in Table 4.

TABLE 4

Catalytic performance of the catalyst obtained in Example 10

| Catalyst | Conversion (%) | ROH selectivity (%) |
|---|---|---|
| $Al_2O_3$/300ZnO/50Cu/0$Al_2O_3$/50Fe/300$Al_2O_3$ | 32.34 | 85.8 |
| $Al_2O_3$/300ZnO/50Cu/10$Al_2O_3$/50Fe/300 $Al_2O_3$ | 46.39 | 90.3 |
| $Al_2O_3$/300ZnO/50Cu/20$Al_2O_3$/50Fe/300 $Al_2O_3$ | 40.95 | 86.6 |
| $Al_2O_3$/300ZnO/50Cu/30$Al_2O_3$/50Fe/300 $Al_2O_3$ | 35.87 | 87.9 |
| $Al_2O_3$/300ZnO/50Cu/50$Al_2O_3$/50Fe/300 $Al_2O_3$ | 30.64 | 85.6 |
| $Al_2O_3$/300ZnO/50Cu/100$Al_2O_3$/50Fe/300$Al_2O_3$ | 27.91 | 84.8 |

It can be seen from the test results in Table 4 that the CO conversion and the distance between the two active metal layers of Fe and Cu exhibit a volcanic relationship, and the distance between Fe and Cu is too close or too far to favor the synergistic catalysis of the two active components, $Al_2O_3$/300ZnO/50Cu/10 $Al_2O_3$/50Fe/300$Al_2O_3$ catalyst has the highest activity and the highest conversion of carbon monoxide, reaching 46%, the space-time yield of lower alcohol ($C_1$-$C_4$) ROH is 0.21 g·gcat$^{-1}$·h$^{-1}$.

Example 11

A multi-sandwich composite catalyst was prepared in the same manner as in Example 1, and the composition of the catalyst was 300$TiO_2$/300Ni/10$TiO_2$/20Pt/300$TiO_2$. The catalytic performance of the catalyst was tested in the same manner as in Example 1, and the test results are shown in Table 5.

Comparative Example 1

A tube-in-tube structure catalyst was prepared in the same manner as in Example 1, except that the deposited interlayer oxide was replaced with polyimide, and the polyimide was deposited with pyromellitic dianhydride (PMDA) and ethylenediamine (EDA) as the precursor, the deposition temperature was 175° C., the PMDA temperature was 170° C., the pulse time was 10 s, the diffusion time was 20 s, the purge time was 30 s, the EDA pulse time was 0.2 s, the diffusion time was 20 s, the purge time was 30 s. 100 cycles of polyimide (PI) were deposited to obtain the same system tube-in-tube structure having a composition of $300TiO_2/300Ni/20Pt/300TiO_2$. The catalytic performance of the catalyst was tested in the same manner as in Example 1, and the test results are shown in Table 5.

TABLE 5

Catalytic performance of the catalysts obtained in Example 11 and Comparative Example 1

| Catalyst | Conversion (%) | Selectivity (%) |
|---|---|---|
| Five-sandwich structure $300TiO_2/300Ni/10TiO_2/20Pt/300TiO_2$ | 25.31 | >99 |
| Same system tube-in-tube structure $300TiO_2/300Ni/20Pt/300TiO_2$ | 9.52 | >99 |

It can be seen from the test results of Table 5 that under the same conditions, the catalytic performance of the multi-sandwich composite catalyst having a interlayer between the two active metals prepared by the method provided by the present disclosure is about triple of that of the catalyst of the same tube-in-tube structure.

It can be seen from the above embodiments that the preparation method provided by the present disclosure can achieve precise regulation of the distance between two functional centers of the catalyst at the atomic level by simply changing the thickness of the oxide interlayer; using the above method, embodiments of the present disclosure can produce a multi-metal oxide catalyst with a clear structure and adjustable nano-spatial distances, which can realize the gradient control of different functional centers at the nanometer scale, and construct different functional center combinations and suitable spatial distances according to different reaction characteristics to obtain a high-performance tandem catalyst.

In addition, the multi-sandwich composite catalyst provided by the present disclosure can be repeatedly used and has strong practical value.

What is claimed is:

1. A method for preparing a multi-sandwich composite catalyst comprising:
   sequentially depositing a first layer oxide, a first active metal, an oxide interlayer, a second active metal and a surface oxide on a template; and
   sequentially performing calcination and reduction, thereby obtaining a multi-sandwich composite catalyst;
   wherein the first active metal and the second active metal are different kinds of active metals.

2. The preparation method according to claim 1, wherein the method comprises:
   coating a dispersion of a carrier on a substrate;
   removing the dispersant; and
   obtaining the template;
   wherein the carrier comprises one or more selected from the group comprising carbon nanotubes, carbon nanofibers, aluminum oxide nanowires, porous aluminum oxide spheres, zinc oxide nanowires, zinc oxide nanorods, and iron oxide nanofibers.

3. The preparation method according to claim 2, wherein the dispersion of the carrier uses an organic solvent or water as the dispersant, wherein a mass ratio of the carrier to the dispersant is between 1:3 and 1:20.

4. The preparation method according to claim 2, wherein the first active metal and the second active metal independently comprise nickel, platinum, palladium, rhodium, cobalt, copper or iron.

5. The preparation method according to claim 4, wherein the sequential depositing comprises:
   completing one diffusion-purging as one cycle with an active metal precursor and ozone, wherein a number of cycles of the first active metal and the second active metal deposition is independently 5-600.

6. The preparation method according to claim 5 wherein a temperature of the active metal precursor is 70-100° C., a pulse time of the first active metal precursor is 5-10 s, a diffusion time of the first active metal precursor is 8-12 s, a purge time of the first active metal precursor is 22-27 s; a pulse time of the second active metal precursor is 0.3-0.7 s, a diffusion time of the second active metal precursor is 8-12 s, a purge time of the second active metal precursor is 20-27 s; a pulse time of the ozone is 1-2 s, a diffusion time of the ozone is 8-12 s, and a purge time of the ozone is 22-27 s.

7. The preparation method according to claim 2, wherein the sequential depositing comprises:
   completing one diffusion-purging as one cycle with an oxide precursor and water vapor, wherein a number of cycles of the first layer oxide and the surface oxide deposition is 10-500, and a number of cycles of the oxide interlayer deposition is 1-99.

8. The preparation method according to claim 1, wherein the first active metal and the second active metal independently comprise nickel, platinum, palladium, rhodium, cobalt, copper or iron.

9. The preparation method according to claim 8, wherein the sequential depositing comprises:
   taking an active metal precursor and ozone to complete one diffusion-purging as one cycle, wherein a number of cycles of the first active metal and the second active metal deposition is independently 5-600.

10. The preparation method according to claim 9, wherein a temperature of the active metal precursor is 70-100° C., a pulse time of the first active metal precursor is 5-10 s, a diffusion time of the first active metal precursor is 8-12 s, a purge time of the first active metal precursor is 22-27 s; a pulse time of the second active metal precursor is 0.3-0.7 s, a diffusion time of the second active metal precursor is 8-12 s, a purge time of the second active metal precursor is 20-27 s; a pulse time of the ozone is 1-2 s, a diffusion time of the ozone is 8-12 s, and a purge time of the ozone is 22-27 s.

11. The preparation method according to claim 1, wherein the oxide comprises one or more selected from the group of titanium oxide, aluminum oxide, zirconia, zinc oxide, cerium oxide, indium oxide, and gallium oxide, and silicon oxide.

12. The preparation method according to claim 1, wherein the sequential depositing comprises:
   completing one diffusion-purging as one cycle with an oxide precursor and water vapor, wherein a number of cycles of the first layer oxide and the surface oxide deposition is 10-500, and a number of cycles of the oxide interlayer deposition is 1-99.

13. The preparation method according to claim 12, wherein a temperature of the oxide precursor is 80-100° C., a temperature of the water vapor is independently 10-40° C.; a pulse time of the oxide precursor is 1-2 s, a diffusion time of the oxide precursor is 7-10 s, a purge time is 18-25 s; a pulse time of the water vapor is 0.1-0.2 s, a diffusion time of the water vapor is 7-10 s, and a purge time of the water vapor is 22-27 s.

14. The preparation method according to claim 1, wherein a calcination temperature is 250-900° C., and a calcination time is 0.5-6 hours.

15. The preparation method according to claim 1, wherein a reducing reagent for reduction comprises a mixed gas of hydrogen and argon; wherein a reduction temperature is 250-900° C., and a reduction time is 1-6 hours.

16. A multi-sandwich composite catalyst prepared by the preparation method according to claim 1, which comprises, in order from inside to outside:
   a first oxide layer;
   a first active metal layer;
   an oxide interlayer;
   a second active metal layer; and
   a surface oxide layer;
   wherein the metal in the first active metal layer and the second active metal layer are different kinds of active metals.

17. The multi-sandwich composite catalyst according to claim 16, wherein a thickness of the first oxide layer is 0.5-20 nm; a thickness of the first active metal layer is 0.5-6 nm; a thickness of the oxide interlayer is less than or equal to 10 nm; a thickness of the second active metal layer is 0.5-6 nm; and a thickness of the surface oxide layer is 0.5-20 nm.

18. The multi-sandwich composite catalyst according to claim 16, wherein the multi-sandwich composite catalyst comprises at least one of a $TiO_2/Ni/TiO_2/Pt/TiO_2$ composite catalyst, a $ZrO_2/Ni/ZrO_2/Pt/ZrO_2$ composite catalyst, a $TiO_2/Ni/ZnO/Pt/TiO_2$ composite catalyst, a $TiO_2/Ni/Al_2O_3/Pt/TiO_2$ composite catalyst, a $TiO_2/Ni/Ga_2O_3/Pt/TiO_2$ composite catalyst, a $Al_2O_3/Pd/Al_2O_3/Rh/Al_2O_3$ composite catalyst, a $CeO_2/Pt/Al_2O_3/Co/SiO_2$ composite catalyst, a $Al_2O_3/ZnO/Cu/Al_2O_3/Fe/Al_2O_3$, or a $TiO_2/Cu/Ga_2O_3/Fe/TiO_2$ composite catalyst.

19. A method comprising initiating a tandem catalytic reaction with the multi-sandwich composite catalyst of claim 16.

20. The method of claim 19, wherein a mass ratio of the multi-sandwich composite catalyst to a substrate is between 1:10 and 1:100.

* * * * *